United States Patent
Hampton

(10) Patent No.: US 12,336,842 B2
(45) Date of Patent: Jun. 24, 2025

(54) ANESTHETIZING MONITORING SYSTEM, UNIT AND METHOD THEREFORE

(71) Applicant: Senzime AB, Uppsala (SE)

(72) Inventor: David Robert Hampton, Woodinville, WA (US)

(73) Assignee: Senzime AB, Uppsala (SE)

( * ) Notice: Subject to any disclaimer, the term of this patent is extended or adjusted under 35 U.S.C. 154(b) by 749 days.

(21) Appl. No.: 16/981,320

(22) PCT Filed: Mar. 11, 2019

(86) PCT No.: PCT/SE2019/050220
§ 371 (c)(1),
(2) Date: Sep. 16, 2020

(87) PCT Pub. No.: WO2019/177526
PCT Pub. Date: Sep. 19, 2019

(65) Prior Publication Data
US 2021/0007661 A1    Jan. 14, 2021

(30) Foreign Application Priority Data
Mar. 16, 2018   (SE) .................................. 1850294-8

(51) Int. Cl.
*A61B 5/00* (2006.01)
*A61B 5/11* (2006.01)
*A61B 5/389* (2021.01)

(52) U.S. Cl.
CPC .......... *A61B 5/4821* (2013.01); *A61B 5/0017* (2013.01); *A61B 5/1106* (2013.01);
(Continued)

(58) Field of Classification Search
CPC ............................................. A61B 5/00–7495
See application file for complete search history.

(56) References Cited

U.S. PATENT DOCUMENTS

| | | |
|---|---|---|
| 5,966,684 A | 10/1999 | Richardson et al. |
| 6,306,100 B1 | 10/2001 | Prass |
| (Continued) | | |

FOREIGN PATENT DOCUMENTS

| | | |
|---|---|---|
| EP | 0 025 222 A2 | 3/1981 |
| EP | 2 016 894 A1 | 1/2009 |
| WO | 2018/001929 A1 | 1/2018 |

OTHER PUBLICATIONS

International Search Report and Written Opinion for corresponding International Patent Application No. PCT/SE2019/050220 dated May 15, 2019.

(Continued)

*Primary Examiner* — Matthew Kremer
*Assistant Examiner* — Evelyn Grace Park
(74) *Attorney, Agent, or Firm* — Renner, Otto, Boisselle & Sklar, LLP

(57) ABSTRACT

The invention relates to a method (400) performed by an anesthetizing monitoring unit (110) configured to generating an improved evoked electromyography response signal ($\Sigma_{Response}$), the method comprising transmitting (515) a stimuli signal ($S_{Stimuli}$) using an output port (112) of the anesthetizing monitoring unit (110), receiving (525) an evoked electromyography, EMG, response signal ($S_{Response}$), having a duration ($T_{Response}$), in response to the transmitted stimuli signal ($S_{Stimuli}$) using an input port (111) of the anesthetizing monitoring unit (110), estimating (535) a periodic noise waveform ($S_{Periodic}$), having the duration ($T_{Response}$), by using temporal segments of a noise signal ($S_{Noise}$), generating (545) the improved response signal ($\Sigma_{Response}$) by subtracting the noise waveform from the response signal ($S_{Response}$). The invention further relates to an anesthetizing monitoring unit (110) and an anesthetizing monitoring system (100).

13 Claims, 6 Drawing Sheets

(52) U.S. Cl.
CPC ............ *A61B 5/389* (2021.01); *A61B 5/7203* (2013.01); *A61B 5/742* (2013.01)

(56) References Cited

U.S. PATENT DOCUMENTS

| | | |
|---|---|---|
| 6,625,481 B2 | 9/2003 | Bennett et al. |
| 2007/0083128 A1 | 4/2007 | Cote et al. |
| 2007/0270918 A1 | 11/2007 | De Bel et al. |
| 2008/0051673 A1 | 2/2008 | Kong et al. |
| 2013/0204155 A1* | 8/2013 | Brull .................... A61B 5/4821 600/546 |
| 2017/0245776 A1* | 8/2017 | Kurtz .................... A61B 5/377 |
| 2018/0256097 A1* | 9/2018 | Bray .................... A61B 5/7282 |

OTHER PUBLICATIONS

Ungureanu, et al., "Basic Aspects Concerning the Event-Synchronous Interference Canceller," IEEE Transactions on Biomedical Engineering, vol. 53, No. 11, pp. 2240-2247, Nov. 2006.
Travis, et al., "A comparison of adaptive and notch filtering for removing electromagnetic noise from monopolar surface electromyographic signals," IOP Publishing, Physiological Measurement, Physiol. Meas. 30, 2009, pp. 353-361, doi: 10.1088/0967-3334/30/4/001.

* cited by examiner

ANESTHETIZING MONITORING SYSTEM, UNIT AND METHOD THEREFORE

TECHNICAL FIELD

The present disclosure relates to anesthetizing monitoring systems, in particular anesthetizing monitoring systems capable of generating or rendering an improved evoked electromyography response signal.

BACKGROUND

In hospitals around the world, patients are administered muscle relaxants also called neuromuscular blocking agents, NMBAs, which inhibit neuromuscular transmission. These relaxant agents decrease muscle tension and suppress reflex contractions. In particular non-depolarizing agents of NMBAs have an effect only for a certain number of minutes, so they may have to be administered repeatedly, and the dose needs to be titrated appropriately, to maintain a desired concentration level or blood concentration throughout a surgical procedure.

It is desirable that the effects of the drugs completely dissipate once the surgical procedure is complete and the patient is in recovery, e.g. so that patients are able to breathing on their own (independently and spontaneously). Reversal drugs (e.g. anticholinesterases) can be administered to speed-up recovery from muscle relaxants, but must also be administered in a controlled manner over time as reversal drugs can slow the heart to dangerous levels (bradycardia), and can have a host of other unpleasant side effects.

Neuromuscular monitoring systems using evoked electromyography, EMG, have been proposed to give an indication of the degree of neuromuscular function or, equivalently, the depth of muscular block. Evoked EMG involves sending a stimuli signal to stimulating electrodes positioned on the patient's body and monitoring the response from receiving electrodes also positioned on the patient's body.

An example of such a system is provided in the document EP0025222 A2, which relates to the technical field of determining a degree of neuromuscular blockage, and shows a device providing an indication of muscular blockage.

A problem with such systems is that the EMG response signal may comprise a periodic noise component, which varies with each patient and/or over time, depending on the environmental conditions. This degrades or obscures the response signal and thus reduces the accuracy and reproducibility of the determination of the muscular function or block. This is especially a problem as the response signal amplitude diminishes with the application of drugs. In one example, the periodic noise appears as an interfering signal such that the current amplitude of the response signal appears as a current pulse response corrupted by varying or non-constant amplitude.

Thus, there is a need for an improved system, unit and method for anesthetizing monitoring.

OBJECTS OF THE INVENTION

An objective of embodiments of the present invention is to provide a solution which mitigates or solves the drawbacks described above.

SUMMARY OF THE INVENTION

The above and further objectives are achieved by the subject matter described herein. Further advantageous implementation forms of the invention are described herein.

According to a first aspect of the invention, the above mentioned objectives are achieved by a method performed by an anesthetizing monitoring unit configured to generating an improved evoked electromyography response signal, the method comprises transmitting a stimuli signal using an output port of the anesthetizing monitoring unit, receiving an evoked electromyography, EMG, response signal, having a duration, in response to the transmitted stimuli signal using an input port of the anesthetizing monitoring unit, estimating a periodic noise waveform, having the duration, by using the temporal segments of a noise signal, and generating the improved response signal by subtracting the noise waveform from the response signal.

At least one advantage of this embodiment is that an improved response signal is obtained, thus providing a better indication of an anesthetized patients state.

According to a second aspect of the invention, the above mentioned objectives are achieved by an anesthetizing monitoring unit, the anesthetizing monitoring unit comprising an input port, an output port, and processing circuitry being configured to perform the method according to the first aspect.

According to a third aspect of the invention, the above mentioned objectives are achieved by an anesthetizing monitoring system, the anesthetizing monitoring system comprising an anesthetizing monitoring unit comprising an input port and an output port, stimulating electrodes electrically coupled to the output port and being configured to receive a stimuli signal from the output port and deliver the stimuli signal to the anesthetized patient, receiving electrodes electrically coupled to the input port and being configured to obtain an evoked electromyography, EMG, response signal, in response to the stimuli signal and a noise signal, from the anesthetized patient, the anesthetizing monitoring unit being configured to perform the method according to the first aspect.

The advantages of the second and third aspects are the same as for the first aspect.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly

Figure 1:
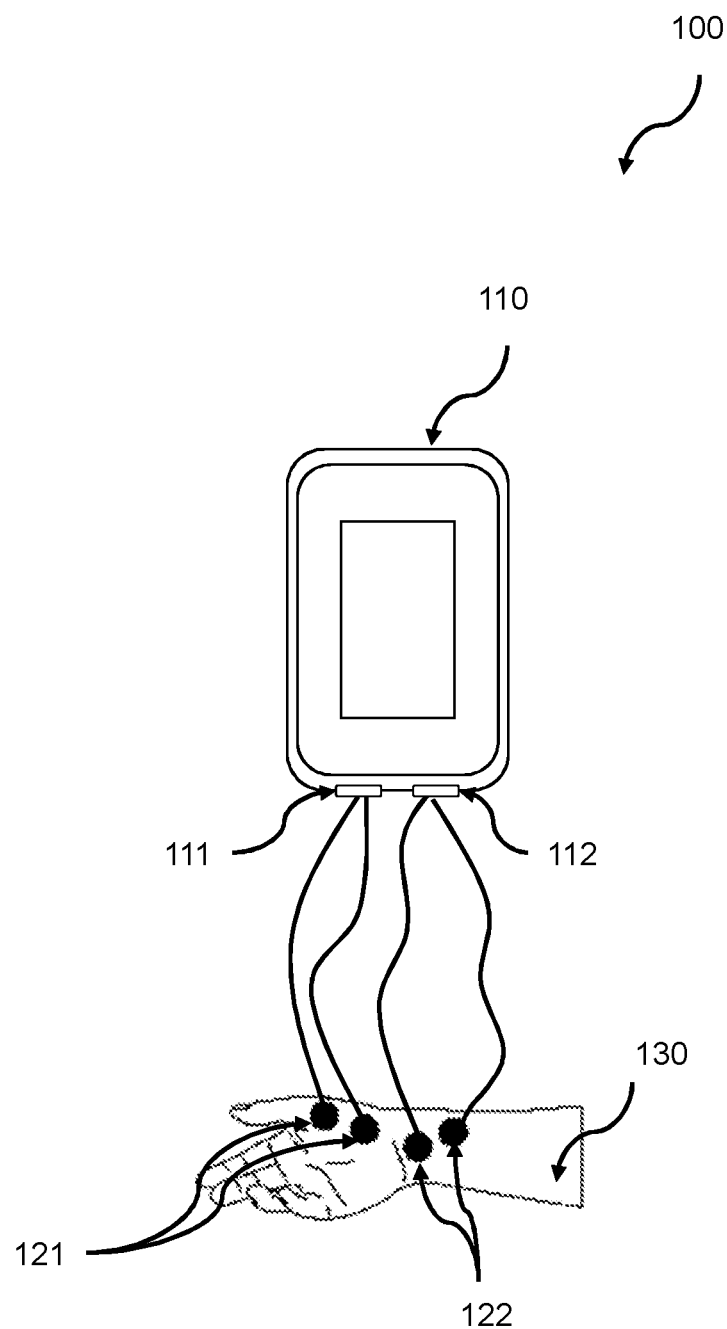
FIG. 1 shows an anesthetizing monitoring system according to one or more embodiments of the present invention.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

DETAILED DESCRIPTION

An "or" in this description and the corresponding claims is to be understood as a mathematical OR which covers "and" and "or", and is not to be understand as an XOR (exclusive OR). The indefinite article "a" in this disclosure and claims is not limited to "one" and can also be understood as "one or more", i.e., plural.

The term anesthetizing monitoring unit signifies herein a unit comprising processing circuitry, such as a processor and coupled memory, adapted for or suitable to be used in a hospital environment, e.g. when performing or recovering from surgery. Examples may include a dedicated computer system, an Electronic Control Unit, a server, a tablet, a smart watch or a smartphone.

The term stimuli signal signifies herein a signal delivered to an anesthetized patient in order to stimulate a motor nerve. The stimuli signal may e.g. be in the form of a pulse in a pulse wave or pulse train pulse or a plurality of pulse wave or pulse train pulses having voltage or current amplitude $A_{Stimuli}$. The stimuli signal is typically delivered to stimulating electrodes 122 attached to an anesthetized patient 130.

The term evoked electromyography, EMG, response signal $S_{Response}$ signifies herein a signal received in response to the transmitted stimuli signal $S_{Stimuli}$. The response signal may e.g. be in the form of a sinusoidal signal, a pulse wave or pulse train pulse or a plurality of pulse wave or pulse train pulses having voltage and/or current amplitude $A_{Response}$. The response signal is typically obtained from receiving electrodes 121 attached to an anesthetized patient 130.

In one example, a subject having been administered a muscle relaxant agent includes stimulating a motor nerve with stimuli signal. After each stimulus of the motor nerve, the muscle response in the muscle(s) innervated by the stimulated motor nerve is recorded as a response signal $S_{Response}$, e.g. to provide an assessment of neuromuscular function or blockade in the subject. Each stimuli signal is sufficient to cause an evoked muscle response signal under normal physiological conditions. As muscle relaxants are administered to a subject, the amplitude $A_{Response}$ of the evoked muscle response signal decreases. The amplitude $A_{Response}$ decreases relative historical or previously detected response signals or is decreased or reduced to a level where no response signal amplitude $A_{Response}$ can be detected.

The term "configured to" may be used interchangeably with "adapted to" or "operative to" in the disclosure herein.

The term "memory" may be used interchangeably with "computer readable medium" or "non-transitory computer readable medium" in the disclosure herein.

Provided in the present disclosure are systems, units and methods for generating an improved evoked electromyography response signal, e.g. by monitoring neuromuscular function or blockade of muscles in patients being administered muscle relaxants such as a neuromuscular blocking agent and/or a depolarizing agent and/or a non-depolarizing agent.

FIG. 1 shows an anesthetizing monitoring system 100 according to one or more embodiments of the present invention. The anesthetizing monitoring system 100 may comprise an anesthetizing monitoring unit 110 provided with an input port 111 and an output port 112 according to embodiments described herein. The anesthetizing monitoring system 100 may further comprise stimulating electrodes 122 configured to be electrically couplable to the output port 112 and being configured to receive a stimuli signal $S_{Stimuli}$ from the output port 112 and deliver the stimuli signal $S_{Stimuli}$ to the anesthetized patient 130. The anesthetizing monitoring system 100 may further comprise receiving electrodes 121 configured to be electrically couplable to the input port 111 and being configured to obtain an evoked electromyography, EMG, response signal $S_{Response}$, in response to the stimuli signal $S_{Stimuli}$, obtained from the anesthetized patient 130 and/or to obtain a noise signal $S_{Noise}$ from the anesthetized patient 130.

Figure 2A:
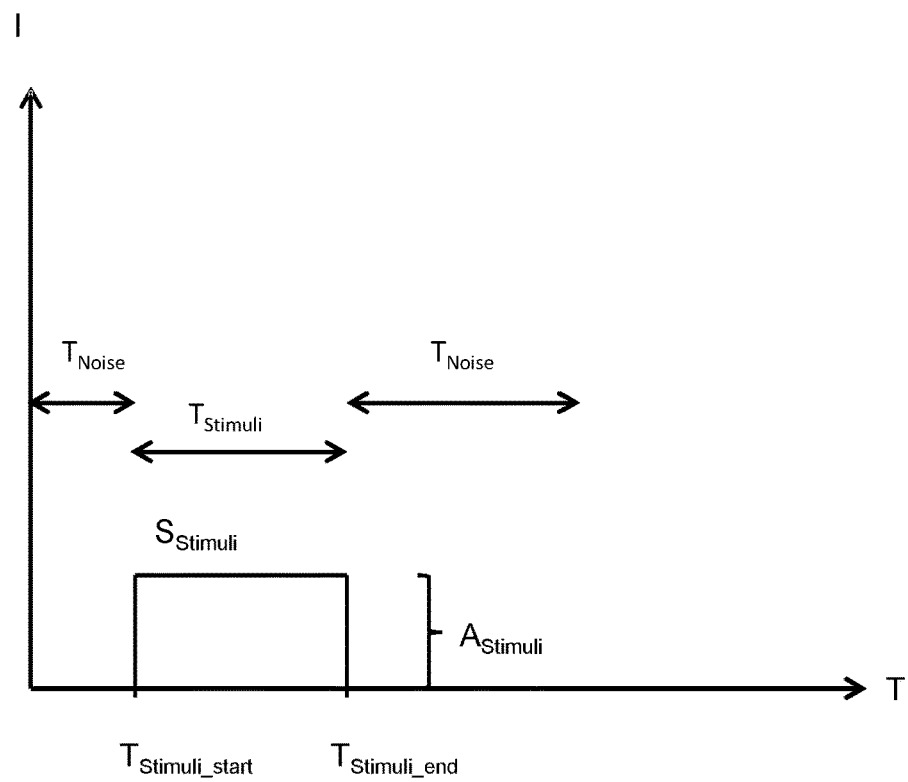
FIG. 2A illustrates a signal diagram of a stimuli signal according to one or more embodiments of the present invention.

FIG. 2A illustrates a signal diagram of a stimuli signal according to one or more embodiments of the present invention. Current amplitude (I) is shown on the vertical axis of the diagram and time (T) is shown on the horizontal axis of the diagram. It is understood that the amplitude could also signify voltage and a similar diagram could be constructed showing voltage (U) on the vertical axis of the diagram. At a first time instant $T_{Stimuli\_start}$, the stimuli signal $S_{Stimuli}$ is transmitted using the output port 112 of the anesthetizing monitoring unit 110. The stimuli signal $S_{Stimuli}$ typically continues or remains with a constant current and/or voltage amplitude until a second time instant $T_{Stimuli\_end}$, i.e. the stimuli signal $S_{Stimuli}$ have duration of $T_{Stimuli}$. The stimuli signal $S_{Stimuli}$ typically has a constant current and/or voltage amplitude of $A_{Stimuli}$. As described further in relation to FIG. 1, the stimuli signal $S_{Stimuli}$ is delivered to the anesthetized patient 130 by stimulating electrodes 122 attached to the anesthetized patient 130. The stimuli signal $S_{Stimuli}$ may comprise a single pulse, such as a pulse of a pulse wave or pulse train, or a plurality of current pulses also referred to as a repeated pulse train. Alternative locations of an adjacent time interval $T_{Noise}$, excluding or not overlapping with the stimuli signal interval $T_{Stimulus}$, is further shown.

Figure 2B:
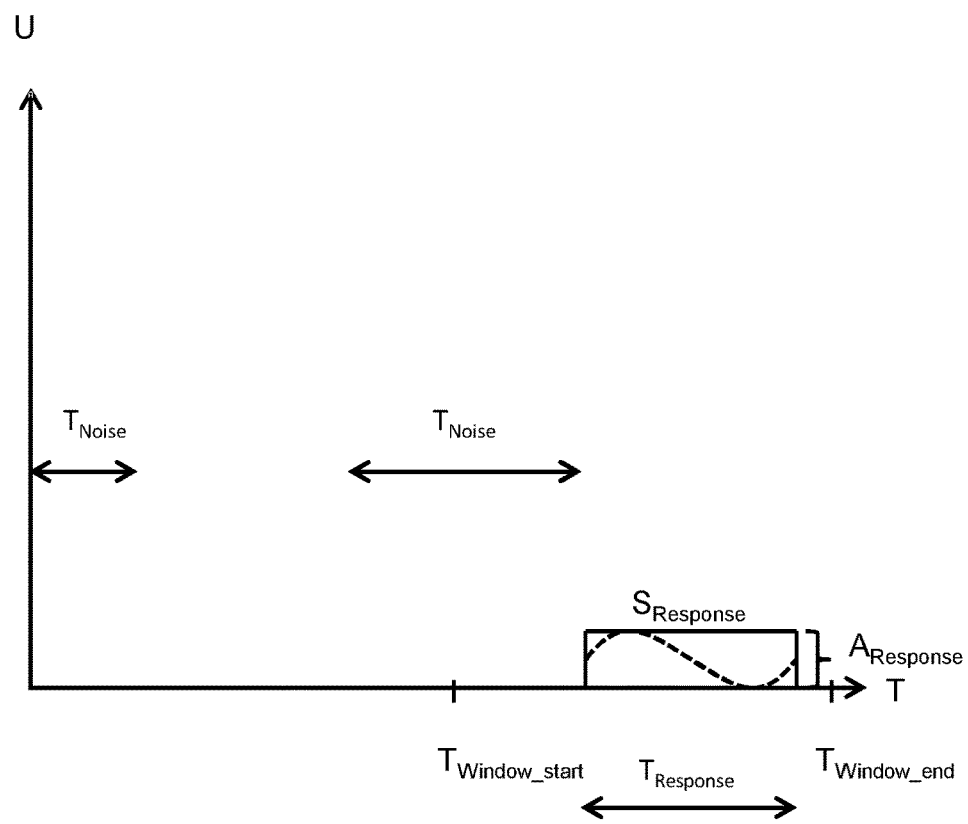
FIG. 2B illustrates a signal diagram of a response signal according to one or more embodiments of the present invention.

FIG. 2B illustrates a signal diagram of a response signal according to one or more embodiments of the present invention. Voltage amplitude (U) of the response signal is shown on the vertical axis of the diagram and time (T) is shown on the horizontal axis of the diagram. After transmission of the stimuli signal Stimuli and/or one or more pulses comprised in the stimuli signal $S_{Stimuli}$, an evoked electromyography, EMG, response signal $S_{Response}$ in response to the transmitted stimuli signal $S_{Stimuli}$ is then received. The response signal $S_{Response}$ may be in the form of a pulse having amplitude $A_{Response}$ or a single cycle of a sinusoid signal, with the amplitude $A_{Response}$ being measured between the positive and negative peak of the sinusoid signal.

The response signal $S_{Response}$ is typically time synchronized to the stimuli signal $S_{Stimuli}$, and detected within a time window between $T_{Window\_start}$ and $T_{Window\_end}$. The response signal $S_{Response}$ has duration of $T_{Response}$, which is substantially the same as the duration of the stimuli signal $S_{Stimuli}$ from $T_{Stimuli\_start}$ to $T_{Stimuli\_end}$. The response signal $S_{Response}$ has ideally either constant amplitude $A_{Response}$ when having a pulse shape or follows the amplitude of a typical sinusoid signal when having the sinusoidal shape. As described further in relation to FIG. 1, the response signal $S_{Response}$ is obtained from the anesthetized patient 130 by receiving electrodes 121 attached to the anesthetized patient 130. The response signal $S_{Response}$ is received using the input port 111 of the anesthetizing monitoring unit 110. Optionally, an anesthetized patient state may then be determined by determining a neuromuscular function value using properties of the stimuli signal $S_{Stimuli}$ and the response signal $S_{Response}$, as further described in relation to FIG. 5.

Alternative locations of an adjacent time interval $T_{Noise}$, excluding or not overlapping with the stimuli signal interval $T_{Stimulus}$ and/or the response signal interval $T_{Response}$ is further shown in FIG. 2A. In embodiments described herein, a noise signal $S_{Noise}$ may be detected and/or obtained during the adjacent time interval $T_{Noise}$.

Figure 3:
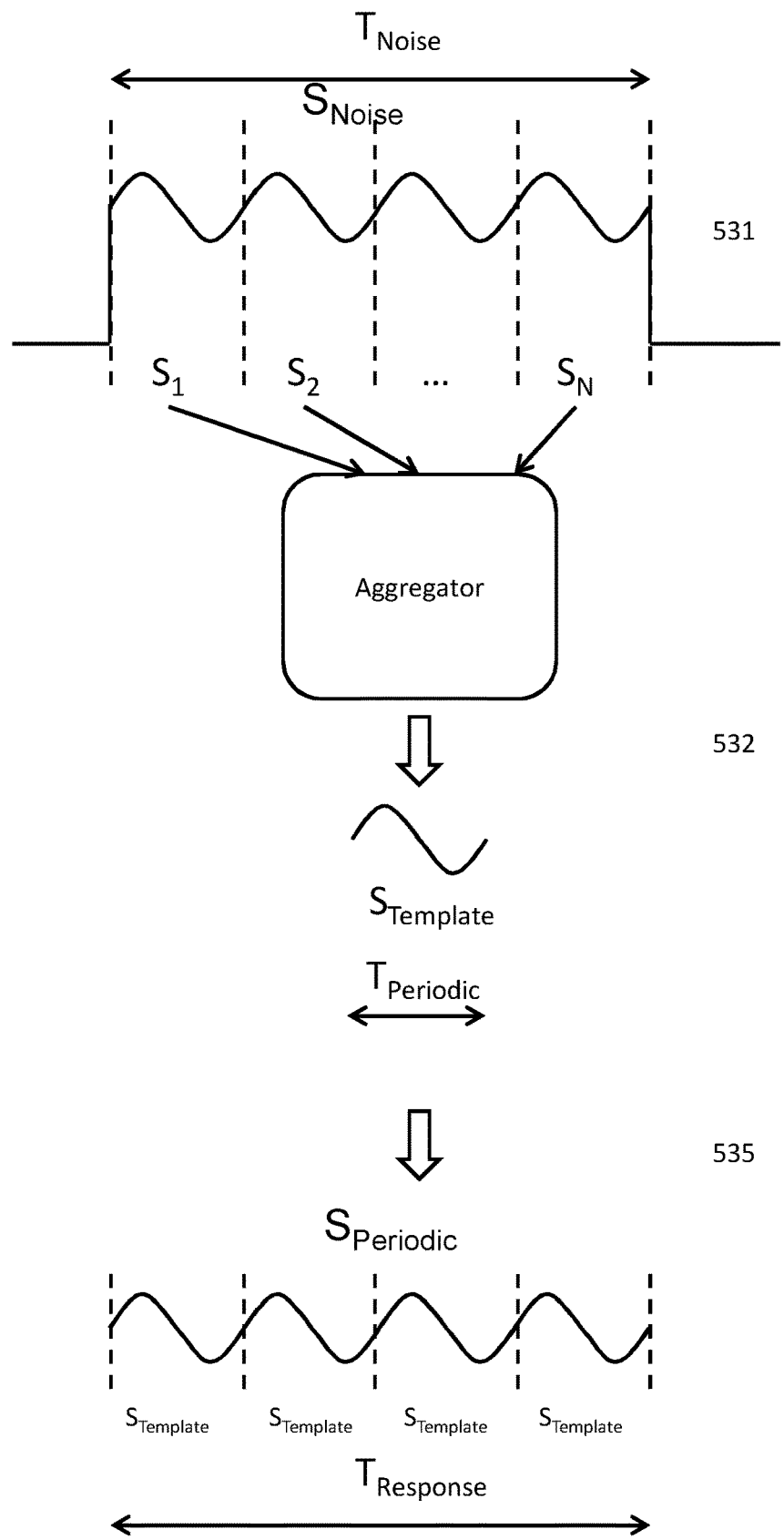
FIG. 3 illustrates a step of estimating a periodic noise waveform according to one or more embodiments of the present invention.

FIG. 3 illustrates a step of estimating 535 a periodic noise waveform $S_{Periodic}$ according to one or more embodiments of the present invention.

The inventor has realized that if the waveform of the periodic noise is assumed to be stationary, with constant periodic noise characteristics within a longer time interval encompassing or including the stimuli signal interval $T_{Stimulus}$ and response signal interval $T_{Response}$, then the periodic noise characteristics can be estimated as a periodic noise signal $S_{Periodic}$ using the noise signal $S_{Noise}$ detected within an adjacent time interval $T_{Noise}$, the adjacent time interval $T_{Noise}$ excluding or not overlapping with the stimuli signal interval $T_{Stimulus}$ and response signal interval $T_{Response}$.

Due to the fact that the frequency content of the waveform of periodic noise is typically higher than a frequency represented by the inverse of the duration of the periodic noise signal $1/S_{Periodic}$, the inventor realized that the periodic noise signal $S_{Periodic}$ comprises repeating segments or multiple periods of noise each having the duration of $T_{Periodic}$, which repeats itself both within response signal interval $T_{Response}$ and within the longer time interval. These repeating segments may be estimated as $S_{Template}$.

The detected noise signal $S_{Noise}$ may therefore first be split 531 into a number N of temporal segments ($S_1, S_2, \ldots, S_N$), each of duration $T_{Periodic}$. In one example, this may comprise sampling the noise signal $S_{Noise}$ to a number L of bits, and splitting the L bits into N segments, each having a length of L/N bits.

The number of and/or duration of and/or length of the N segments may be selected using the strongest periodic noise component, e.g. 50 Hz contribution from the electric power grid, e.g. duration of 1/50 seconds. The strongest periodic noise component may e.g. be obtained by performing a frequency analysis or frequency transform, such as a Fourier transform, of the response signal $S_{Response}$ to identify the strongest or most dominant periodic noise component.

In other words, identifying a strongest frequency component of the Fourier transform as the periodic noise component.

Figure 5:
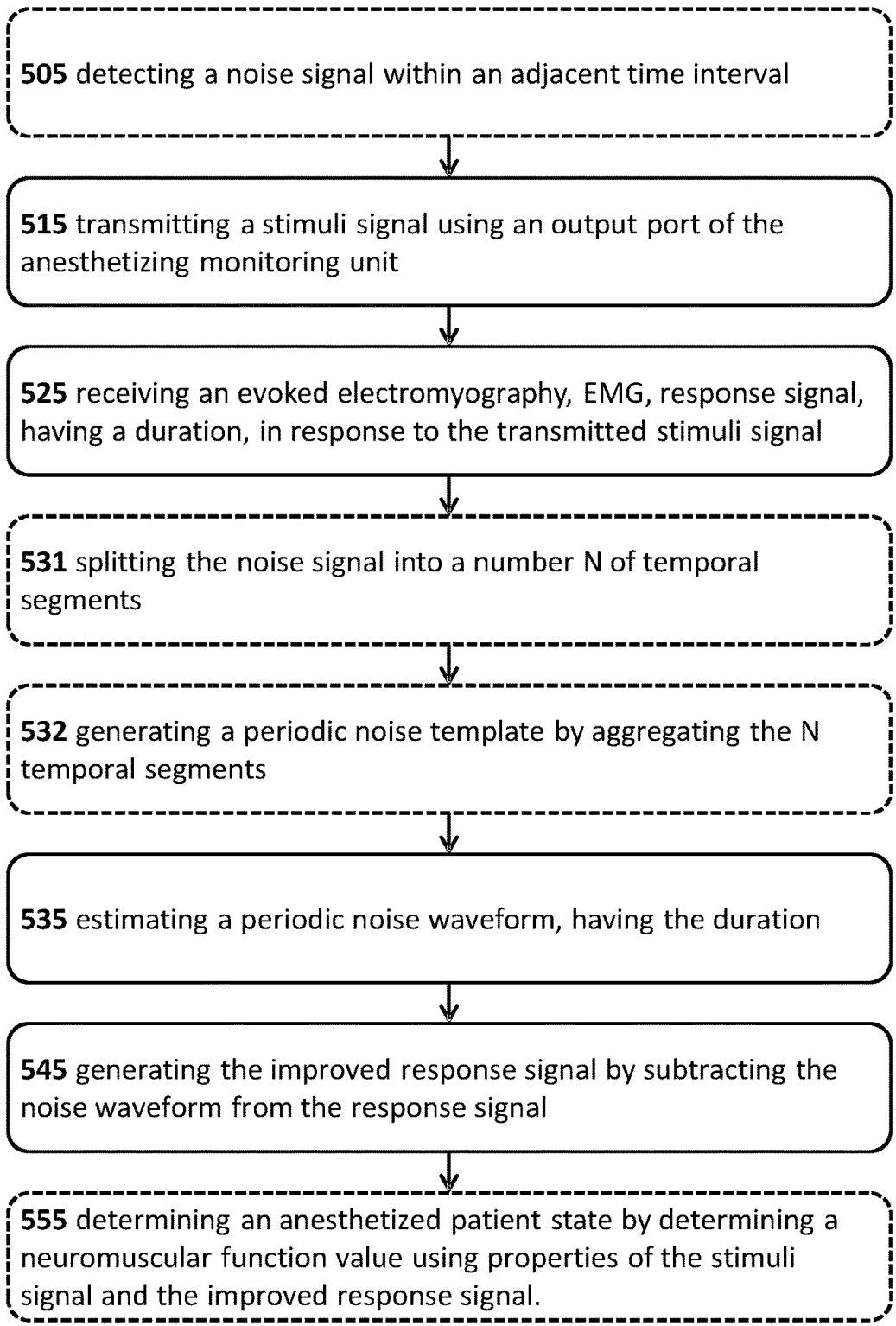
FIG. 5 shows a block diagram of a method according to one or more embodiments of the present invention.

A periodic noise template $S_{Template}$ may then be generated 532 by aggregating the N temporal segments ($S_1, S_2, \ldots, S_N$), e.g. by averaging N temporal segments ($S_1, S_2, \ldots, S_N$) using an aggregator module or function implemented by the processing circuitry 103, further described in relation to FIG. 5.

In one example, the N temporal segments ($S_1, S_2, \ldots, S_N$) are averaged sample by sample to generate a periodic noise template $S_{Template}$ having a duration or length of L/N bits. In other words, the first sample in each of the segments are averaged to generate the first value of the periodic noise template $S_{Template}$, the second sample in each of the segments are averaged to generate the second value of the periodic noise template $S_{Template}$ and so forth. A periodic noise waveform $S_{Periodic}$ having a duration of $T_{Response}$ may then be estimated 535 by subsequently repeating and/or appending the periodic noise template $S_{Template}$ N times to obtain a periodic noise waveform $S_{Periodic}$ having a duration equal to or substantially equal to the duration $T_{Response}$ of the response signal $S_{Response}$.

An improved response signal $\Sigma_{Response}$ may then be generated or calculated by subtracting the periodic noise waveform $S_{Periodic}$ from the current response signal $S_{Response}$.

In one example, the estimated periodic noise waveform $S_{Periodic}$ may then optionally be time aligned with and subtracted from the original $S_{Response}$, e.g. sample by sample, to recover the uncorrupted signal or improved response signal $\Sigma_{Response}$, i.e. the current response signal $S_{Response}$ comprising both the desired response and the periodic noise is improved by removing or reducing the periodic noise by subtracting the periodic noise waveform $S_{Periodic}$ from the current response signal $S_{Response}$.

Figure 4:
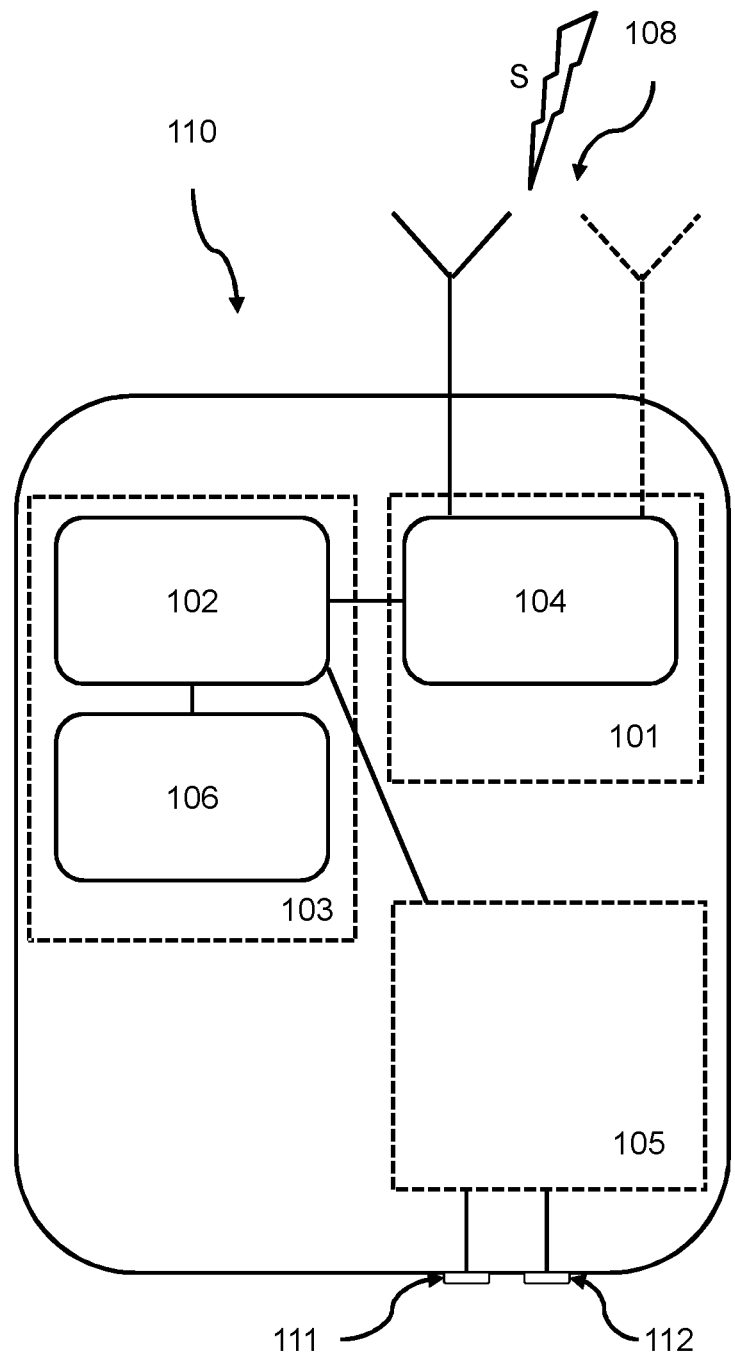
FIG. 4 illustrates an anesthetizing monitoring unit according to one or more embodiments of the present invention.

FIG. 4 illustrates an anesthetizing monitoring unit 110 according to one or more embodiments of the present invention. The anesthetizing monitoring unit 110 comprises processing circuitry 103. The processing circuitry 103 may comprise a processor 102 communicatively coupled to a memory 106, said memory 106 comprising instructions executable by said processor, whereby said anesthetizing monitoring unit 110 is operative to perform the method of any of the embodiments described herein.

The processing circuitry 103 may in one optional embodiment be communicatively coupled to a communication interface 101, e.g. comprising one or more transceivers 104. The communication interface 101 may be operative to receive information, such as a data packet, from the processor 102 and generate a wireless signal S for a wireless communication network or to receive the wireless signal S for a wireless communication network 231-233. The communication interface 101 may further be operative to demodulate and/or decode the wireless signal S to a data packet and send to the processor 102. Further, the anesthetizing monitoring unit 110 may further comprise one or more optional antennas 108, as shown in FIG. 4. The antenna/s 108 is/are coupled to the transceiver/s 104 and is/are configured to transmit/emit or receive wireless signals S for a wireless communication network, e.g. transmit a data packet included or comprised in the wireless signal S. The data packet may comprise a representation of the stimuli signal, the response signal or any other data. The processor and/or a processor unit 102 may be, e.g. processing circuitry and/or a central processing unit and/or processor modules and/or multiple processors configured to cooperate with each-other. The memory 106 may comprise of essentially any suitable memory, such as a ROM (Read-Only Memory), a PROM (Programmable Read-Only Memory), an EPROM (Erasable PROM), a Flash memory, an EEPROM (Electrically Erasable PROM), or a hard disk drive. The communication interface 101 may be configured to send or receive data to other nodes such as servers or other anesthetizing monitoring units. E.g. transmitting or receiving an improved response signal $\Sigma_{Response}$, anesthetized patient state/s, neuromuscular function value/s or properties of the stimuli signal $S_{Stimuli}$ and/or the response signal $S_{Response}$.

The processing circuitry 103 may in one embodiment be communicatively coupled to a measurement interface 105. The measurement interface 105 is further coupled or communicatively coupled to the input port 111 and the output port 112. The measurement interface 105 is configured to transmit the stimuli signal $S_{Stimuli}$ in response to a control signal received from the processing circuitry 103. The control signal may e.g. comprise properties of the stimuli signal $S_{Stimuli}$, such as the amplitude $A_{Stimuli}$. The measurement interface 105 is further configured to receive the response signal $S_{Response}$, detecting properties of the response signal $S_{Response}$ such as the amplitude $A_{Response}$, and send the properties of the response signal $S_{Response}$ to the processing circuitry 103. The properties of the response signal $S_{Response}$ may include one or more amplitude values $A_{Response}$. The measurement interface 105 may further be configured to send the response signal $S_{Response}$ to the processing circuitry 103 and/or to generate the improved response signal $\Sigma_{Response}$ and send to the processing circuitry 103.

In one or more embodiments, the anesthetizing monitoring unit 110 may further comprise an input device (not shown in the figure), configured to receive input or indications from a user and send a user-input signal indicative of the user input or indications to the processing circuitry 103.

In one or more embodiments the anesthetizing monitoring unit 110 may further comprise a display (not shown in the figure) configured to receive a display signal indicative of rendered objects, such as text or graphical user input objects, from the processing circuitry 103 and to display the received signal as objects, such as text or graphical user input objects.

In one embodiment, the display is integrated with the user input device and is configured to receive a display signal indicative of rendered objects, such as text or graphical user input objects, from the processing circuitry 103 and to display the received signal as objects, such as text or graphical user input objects, and/or configured to receive input or indications from a user and send a user-input signal indicative of the user input or indications to the processing circuitry 103.

In embodiments, the processing circuitry 103 is further communicatively coupled to the input device and/or the display.

FIG. 5 shows a block diagram of a method 500 according to one or more embodiments of the present invention. The method 500 is performed by an anesthetizing monitoring unit 110 configured to generate an improved evoked electromyography response signal $\Sigma_{Response}$.

In a first example, the improved evoked electromyography response signal $\Sigma_{Response}$ includes eliminated and/or substantially reduced levels of periodic noise components compared to the received response signal $S_{Response}$.

The method 500 comprises:

OPTIONAL STEP 505: obtaining or detecting a noise signal $S_{Noise}$ within an adjacent time interval $T_{Noise}$, excluding or not overlapping with the stimuli signal interval $T_{Stimulus}$ and response signal interval $T_{Response}$, as further described in relation to FIGS. 2A and 2B. The adjacent time interval $T_{Noise}$ is typically selected to be adjacent in time to the stimuli signal interval $T_{Stimulus}$ and/or the response signal interval $T_{Response}$. As described further in relation to FIGS. 2A and 2B, the noise signal $S_{Noise}$ may be obtained or detected before STEP 515, between STEP 515 and STEP 525 or immediately after STEP 525.

STEP 515: transmitting the stimuli signal $S_{Stimuli}$ using an output port 112 of the anesthetizing monitoring unit 110. The stimuli signal $S_{Stimuli}$ may be in the form of a pulse wave or pulse train current pulse or a plurality of pulse wave or pulse train current pulses, wherein each pulse e.g. have constant current or voltage amplitude $A_{Stimuli}$. As described further in relation to FIG. 1, the stimuli signal $S_{Stimuli}$ is delivered to the anesthetized patient 130 by stimulating electrodes 122 attached to the anesthetized patient 130.

STEP 525: receiving an evoked electromyography, EMG, response signal $S_{Response}$, having a duration $T_{Response}$, in response to the transmitted stimuli signal $S_{Stimuli}$. As described further in relation to FIG. 1, the response signal $S_{Response}$ is obtained from the anesthetized patient 130 by receiving electrodes 121 attached to the anesthetized patient 130 and received by the input port 111. The properties of the response signal $S_{Response}$ further described in relation to FIG. 2B.

STEP 535: estimating a periodic noise waveform $S_{Periodic}$ having the duration $T_{Response}$. The periodic noise waveform $S_{Periodic}$ may be estimated by using the temporal segments $S_1, S_2, \ldots, S_N$ of the noise signal $S_{Noise}$, as further described in relation to FIG. 3.

STEP 545: generating the improved response signal $\Sigma_{Response}$ by subtracting the periodic noise waveform $S_{Periodic}$ from the response signal $S_{Response}$. The improved response signal $\Sigma_{Response}$ having the amplitude $A_{Response}$.

In one embodiment, the method further comprises the steps:

STEP 531: splitting the noise signal $S_{Noise}$ having the duration off $T_{Noise}$, into a number N of temporal segments $(S_1, S_2, \ldots, S_N)$. The number N of temporal segments $(S_1, S_2, \ldots, S_N)$ typically each having a duration of $T_{Periodic}$.

In one example, this may comprise sampling the noise signal $S_{Noise}$ to a number L of bits, and splitting the L bits into N segments, each having a length of L/N bits. The duration and/or length of the N segments may be selected using the strongest periodic noise component, e.g. 50 Hz contribution from the electric power grid, e.g. a duration $T_{Periodic}$ of 1/50 seconds. The strongest periodic noise component may e.g. be obtained by doing a frequency analysis or frequency transform, such as a Fourier transform, of the response signal $S_{Response}$ to identify the strongest periodic noise component.

In other words, the duration $T_{Periodic}$ is selected using a strongest periodic noise frequency component or component of the noise signal $S_{Noise}$.

STEP 532: generating a periodic noise template $S_{Template}$ by aggregating the N temporal segments $(S_1, S_2, \ldots, S_N)$, e.g. by an aggregator module implemented by the processing circuitry 103, e.g. as an averaging filter. The aggregator module may generate the periodic noise template $S_{Template}$ by averaging the N temporal segments $(S_1, S_2, \ldots, S_N)$, e.g. sample by sample.

In one embodiment, the periodic noise template $S_{Template}$ is generated by averaging discrete samples over the N temporal segments $S_1, S_2, \ldots, S_N$. In one example, the N temporal segments are averaged sample by sample to generate a periodic noise template $S_{Template}$ having a duration or length of L/N bits. In other words, all first samples of each segment are averaged to generate the first value of the periodic noise template $S_{Template}$, all second samples of each segment are averaged to generate the second value of the periodic noise template $S_{Template}$ and so forth.

A periodic noise waveform $S_{Periodic}$ may then be estimated 435 by subsequently repeating or appending the periodic noise template $S_{Template}$ to obtain a periodic noise waveform $S_{Periodic}$, having a duration equal to or substantially equal to the duration $T_{Response}$ of the response signal $S_{Response}$.

In one optional embodiment, the method 500 further comprises:

STEP 550: determining an anesthetized patient state by determining a neuromuscular function value using properties of the stimuli signal $S_{Stimuli}$ and/or the improved response signal $\Sigma_{Response}$. The anesthetized patient state may e.g. be determined as a selection of any of the statuses "normal breathing function", "capable of sustaining breathing", "in need of ventilator", "insufficient anesthetic level", "low anesthetic level" or "sufficient anesthetic level" but not limited thereto.

Additionally or alternatively, the anesthetized patient state may e.g. be determined as a selection of any of the statuses "X % of a reference neuromuscular transmission level" or "N responses out of M transmitted stimuli received" but not limited thereto.

The neuromuscular function value may be determined by stimulating an accessible peripheral motor nerve of the anesthetized patient with the stimuli signal $S_{Stimuli}$ via stimulating electrodes 122. The evoked response, e.g. the evoked response of the skeletal muscle or muscles innervated by the stimulated motor nerve, may then be recorded by the evoked electromyography, EMG, response signal $S_{Response}$. The anesthetized patient state may then be determined by comparing properties of the improved response signal $\Sigma_{Response}$ and/or properties of the stimuli signal $S_{Stimuli}$ and/or properties of historical improved response signals $\Sigma_{Response}$ to threshold values, e.g. predetermined and stored in memory or properties historical improved response signals received prior to the current or latest improved response signal $S_{Response}$.

The properties of the improved response signal $\Sigma_{Response}$ may include amplitude value/s $A_{Response'}$. The neuromuscular function value may determined by comparing a quota of amplitude value/s of the improved response signal $\Sigma_{Response}$ and additional amplitude value/s to a set of predetermined amplitude value/s thresholds, wherein the additional amplitude values are selected from amplitude value/s of the stimuli signal $S_{Stimuli}$ and historical amplitude value/s of the improved response signal $\Sigma_{Response}$. Alternatively or additionally, the anesthetized patient state may then be determined as a ratio of the amplitude values $A_{Stimuli}$, $A_{Response'}$ or a response pulse count and optionally a scaling factor.

In one embodiment, the properties of the stimuli signal $S_{Stimuli}$ and the improved response signal $\Sigma_{Response}$ include amplitude values $A_{Stimuli}$, $A_{Response'}$. The neuromuscular function value may then be determined as a quota of amplitude value/s of the stimuli signal $S_{Stimuli}$ and amplitude value/s of the improved response signal $\Sigma_{Response}$. The anesthetized patient state may then be determined by comparing the quota of amplitude value/s to a set of thresholds. The thresholds may be predetermined and stored in memory or derived from historical response signals received prior to the current or latest response signal $S_{Response}$ or the current or latest improved response signal $\Sigma_{Response}$. E.g. by comparing amplitude value/s to individual historical amplitude value/s or aggregated amplitude value/s, e.g. averaged historical amplitude value/s.

In one example, the set of thresholds include, for the ratio $100*(A_{Response}/A_{Stimuli})$, 0-39% indicating an anesthetized patient state of "in need of ventilator", 40-89% indicating an anesthetized patient state of "capable of sustaining breathing" and ≥90% indicating an anesthetized patient state of "normal breathing function".

In one example, the set of thresholds include, for the ratio $A_{Response}/A_{Stimuli}$, 0-0.39 indicating an anesthetized patient state of "in need of ventilator", 0.40-0.89 indicating an anesthetized patient state of "capable of sustaining breathing" and ≥0.90 indicating an anesthetized patient state of normal breathing function".

In one example, the set of thresholds include, for the ratio $100*(A_{Response}/A_{Stimuli})$, 0-39% indicating an anesthetized patient state of "sufficient anesthetic level", 40-89% indicating an anesthetized patient state of "low anesthetic level" and ≥90% indicating an anesthetized patient state of "insufficient anesthetic level".

In one example, the set of thresholds include, for the ratio $A_{Response}/A_{Stimuli}$, 0-0.39 indicating an anesthetized patient state of "insufficient anesthetic level", 0.40-0.89 indicating an anesthetized patient state of "low anesthetic level" and ≥0.90 indicating an anesthetized patient state of "insufficient anesthetic level".

In one example, the neuromuscular function value is determined as a quota of amplitude values $(A_{Response}/A_{Stimuli})=0.9$ and the anesthetized patient state is determined as 90% of a reference neuromuscular transmission level, the reference level being 100% or full neuromuscular transmission level.

In one example, the neuromuscular function value is determined as a count of two (2) received response pulses out of four (4) transmitted stimuli pulses and the anesthetized patient state is determined as 2 responses out of 4 transmitted stimuli received.

In one example, determining a neuromuscular function value includes stimulating a motor nerve with a plurality of temporally distinct stimuli, e.g. pulses comprised in the stimuli signal $S_{Stimuli}$. After each stimulus of the motor nerve, the muscle response in the muscle(s) innervated by the stimulated motor nerve is recorded as an evoked response comprised in the response signal $S_{Response}$. The recorded evoked muscle responses following the application of the plurality of stimuli are evaluated to provide an anesthetized patient state. Each stimulus of the plurality is sufficient to cause an evoked muscle response under normal physiological conditions. As muscle relaxants are administered to patients, the evoked muscle response decreases. Determining the neuromuscular function value may include determining a ratio of an amplitude of a particular recorded muscle response to the amplitude of a muscle response resulting from any subsequent or previous response pulse to characterize the neuromuscular function value, which is related to the degree of muscle function or blockade. In some implementations, evaluation of the muscle responses may include determining a ratio of the amplitude of a muscle response from a subsequent pulse to the amplitude of the muscle response from a previous pulse. A neuromuscular function value less than 1.0 indicates the presence of neuromuscular blockade in the anesthetized patient.

In one example, one or more of the subsequent pulses do not produce an evoked muscle response. When the subsequent and/or first pulse does not produce an evoked muscle response, the determined ratio is zero indicating presence of neuromuscular blockade in the subject. Optionally, as an alternative or supplemental measure, the number of subsequent pulse evoking a muscle response may be counted and determined as the neuromuscular function value.

In one example, the neuromuscular function value is determined as a ratio of the amplitude of the muscle response related to the fourth pulse to the amplitude of the muscle response related to the first pulse of a plurality of stimuli or pulses comprised in the stimuli signal $S_{Stimuli}$. Although it is not required, in some implementations, the fourth pulse may be the fourth sequential pulse and the first pulse may be the first pulse in the plurality of sequential pulses. Optionally, the ratio is determined as a ratio of the amplitude of the muscle response related to the fifth or greater pulse to the amplitude of the muscle response related to the first pulse. For example, the ratio is optionally determined from the amplitude of the muscle response related to the sixth, seventh, eighth, ninth, or tenth pulse to the amplitude of the muscle response related to the first pulse. Regardless of which number subsequent pulse is used, the ratio is zero if there is no muscle response related to the first and/or the subsequent pulse of the plurality of pulses.

The method optionally further includes identifying one or more stimuli of the plurality of temporally distinct stimuli that caused an evoked muscle response and enumerating them to determine a count. The count can be determined subsequent to determining a zero value ratio. Optionally, the count is zero. A count of zero indicates that none of the one or more of the plurality of stimuli used to determine the count caused an evoked muscle response.

If the ratio or the count is zero, the method optionally comprises stimulating the motor nerve in a tetanic protocol. A tetanic protocol may optionally comprise delivering a plurality of stimuli at a rate that is high enough to cause fusion of the individual evoked muscle responses into a single sustained muscle contraction. Optionally, this may be a rate greater than 30 stimuli per second. A neuromuscular function value based on the ratio of the amplitude of the last evoked response to the amplitude of the first evoked response may be calculated, and a neuromuscular function value greater than 0.9 demonstrates that the anesthetized patient state can be determined to "normal breathing function". Alternatively, because there may be some amplitude variation in the evoked muscle responses at the beginning of the tetanic stimulation, a ratio of the amplitude of any response toward the end of the stimulation to the amplitude of any response toward the beginning of the stimulation may be calculated.

In one embodiment, the motor nerve is optionally stimulated with a plurality of temporally spaced supplemental stimuli or pulses. After each stimulation of the motor nerve, the muscle responses of the muscle innervated by the stimulated motor nerve are recorded. The number of evoked muscle responses produced by the temporally spaced subsequent stimuli is used to determine a post-tetanic count and indicates an "X % of reference neuromuscular transmission", where X % indicates a percentage of the number of evoked muscle responses to the temporally spaced supplemental stimuli or pulses.

In one embodiment, the neuromuscular function value is determined by stimulating a motor nerve to cause an evoked muscle response. The evoked muscle response is recorded. A peak of the recorded evoked muscle response is identified. The amplitude of the peak from a baseline is determined. The measured amplitude from the baseline is compared to a control amplitude, determined from prior stimuli, to indicate a change in the neuromuscular function value is determined or that the desired the neuromuscular function value has been maintained.

In one embodiment, the method 400 further comprises displaying the anesthetized patient state to a user of the anesthetizing monitoring unit 110.

Figure 6:
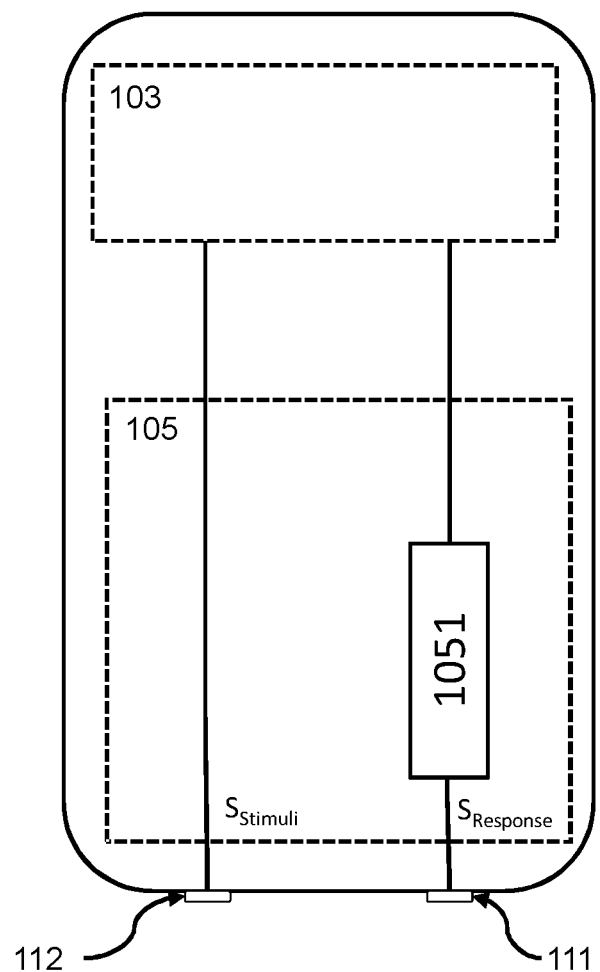
FIG. 6 illustrates an anesthetizing monitoring unit according to one or more embodiments of the present invention.

FIG. 6 illustrates an anesthetizing monitoring unit 110 according to one or more embodiments of the present invention. The measurement interface 105 may further comprise an analog to digital converter, A/D, 1051 configured to receive the response signal $S_{Response}$, sample the response signal $S_{Response}$ to obtain properties of the response signal $S_{Response}$, such as a amplitude value indicative of the improved response signal's amplitude $A_{Response}$. The measurement interface 105 may further be configured to receive the evoked electromyography response signal $S_{Response}$ and generate the improved response signal, e.g. by subtracting the noise waveform from the response signal.

In one embodiment, a computer program is provided comprising computer-executable instructions for causing an anesthetizing monitoring unit (110), when the computer-executable instructions are executed on a processing unit comprised in the anesthetizing monitoring unit (110) to perform the method 500 described herein.

In one embodiment, a computer program product comprising a computer-readable storage medium, the computer-readable storage medium having the computer program above embodied therein. The memory and/or computer-readable storage medium referred to herein may comprise of essentially any memory, such as a ROM (Read-Only Memory), a PROM (Programmable Read-Only Memory), an EPROM (Erasable PROM), a Flash memory, an EEPROM (Electrically Erasable PROM), or a hard disk drive.

Moreover, it is realized by the skilled person that the anesthetizing monitoring unit 110 may comprise the necessary communication capabilities in the form of e.g., functions, means, units, elements, etc., for performing the present solution. Examples of other such means, units, elements and functions are: processors, memory, buffers, control logic, mapping units, multipliers, decision units, selecting units, switches, inputs, outputs, antennas, amplifiers, receiver units, transmitter units, DSPs, MSDs, encoder, decoder, power supply units, power feeders, communication interfaces, communication protocols, etc. which are suitably arranged together for performing the present solution.

Especially, the processor/processing means of the present disclosure may comprise one or more instances of processing circuitry, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processor" and/or "processing means" may thus represent a processing circuitry comprising a plurality of processing circuits, such as, e.g., any, some or all of the ones mentioned above. The processor/processing means may further perform data processing functions for inputting, outputting, and processing of data comprising data buffering and device control functions, such as call processing control, user interface control, or the like.

Finally, it should be understood that the invention is not limited to the embodiments described above, but also relates to and incorporates all embodiments within the scope of the appended independent claims.

The invention claimed is:

1. A method performed by an anesthetizing monitoring unit configured to generate an improved evoked electromyography response signal ($\Sigma_{Response}$), the method comprising:
   generating a single stimuli signal ($S_{Stimuli}$) using the anesthetizing monitoring unit, wherein the single stimuli signal ($S_{Stimuli}$) comprises a single pulse and is configured to stimulate a motor nerve of a patient,
   outputting the generated single stimuli signal ($S_{Stimuli}$) to stimulating electrodes on the patient using an output port of the anesthetizing monitoring unit,
   receiving a single evoked electromyography, EMG, response signal ($S_{Response}$) from receiving electrodes on the patient at an input port of the anesthetizing monitoring unit, having a duration ($T_{Response}$), in response to the outputted stimuli signal ($S_{Stimuli}$), estimating a periodic noise waveform ($S_{Periodic}$), having the duration ($T_{Response}$), based on a noise signal ($S_{Noise}$) by splitting the noise signal ($S_{Noise}$) into temporal segments, wherein:
  the noise signal ($S_{Noise}$) is caused by an electric power grid having a frequency;
  the temporal segments each have a periodic duration ($T_{Periodic}$) matching the frequency of the electric power grid; and
  the temporal segments of the noise signal ($S_{Noise}$) are detected during a time interval ($T_{Noise}$) not overlapping with a stimuli signal interval ($T_{Stimulus}$) of the single stimuli signal ($S_{Stimuli}$) and not overlapping with the duration of the response signal ($T_{Response}$),
generating the improved response signal ($\Sigma_{Response}$) by subtracting the noise waveform from the response signal ($S_{Response}$) to reduce noise in the response signal ($S_{Response}$) caused by the electric power grid,
storing the improved response signal ($\Sigma_{Response}$) in a memory in the anesthetizing monitoring unit, and
presenting the improved response signal ($\Sigma_{Response}$) on a display in the anesthetizing monitoring unit.

2. The method according to claim 1, wherein the step of estimating the periodic noise waveform further comprises:
splitting the noise signal ($S_{Noise}$) into a number N of the temporal segments ($S_1, S_2, \ldots, S_N$),
generating a periodic noise template ($S_{Template}$) by aggregating the N temporal segments ($S_1, S_2, \ldots, S_N$),
wherein the periodic noise waveform ($S_{Periodic}$), is estimated by subsequently repeating the periodic noise template ($S_{Template}$) N times.

3. The method according to claim 2, wherein the periodic noise template ($S_{Template}$) is generated by averaging discrete samples over the N temporal segments ($S_1, S_2, \ldots, S_N$).

4. The method according to claim 2, wherein the periodic duration ($T_{Periodic}$) of each of the temporal segments ($S_1, S_2, \ldots, S_N$) is proportional to the noise signal ($S_{Noise}$).

5. The method according to claim 4, wherein the periodic duration ($T_{Periodic}$) of each of the temporal segments ($S_1, S_2, \ldots, S_N$) is selected using a strongest periodic noise component of the noise signal ($S_{Noise}$).

6. The method according to claim 1, wherein the method further comprises determining an anesthetized patient state by determining a neuromuscular function value using properties of the improved response signal ($\Sigma_{Response}$).

7. The method according to claim 6, wherein the anesthetized patient state is a selection of any of "insufficient anesthetic level", "low anesthetic level", "sufficient anesthetic level", "normal breathing function", "capable of sustaining breathing" or "in need of ventilator".

8. The method according to claim 6, wherein the properties of the improved response signal ($\Sigma_{Response}$) include one or more amplitude values ($A_{Response}$) and wherein the neuromuscular function value is determined by comparing a quota of the one or more amplitude values of the improved response signal ($\Sigma_{Response}$) and one or more additional amplitude values to a set of predetermined amplitude value thresholds, wherein the one or more additional amplitude values are selected from one or more amplitude values of the stimuli signal ($S_{Stimuli}$) and one or more historical amplitude values of the improved response signal ($\Sigma_{Response}$).

9. The method according to claim 8, wherein the set of predetermined amplitude value thresholds are predetermined properties of historical improved response signals received at the anesthetizing monitoring unit prior to the response signal ($S_{Response}$) being received by the anesthetizing monitoring unit, wherein the threshold values are stored in the memory of the anesthetizing monitoring unit.

10. An anesthetizing monitoring system configured to determine a state of an anesthetized patient, the anesthetizing monitoring unit comprising:
an anesthetizing monitoring unit comprising an input port and an output port,
stimulating electrodes electrically coupled to the output port and being configured to receive a stimuli signal ($S_{Stimuli}$) from the output port and deliver the stimuli signal ($S_{Stimuli}$) to the anesthetized patient,
receiving electrodes electrically coupled to the input port and being configured to obtain an evoked electromyography, EMG, response signal ($S_{Response}$), in response to the stimuli signal ($S_{Stimuli}$) and a noise signal ($S_{Noise}$), from the anesthetized patient, the anesthetizing monitoring unit being configured to perform the method according to claim 1.

11. The method according to claim 1, wherein the temporal segments of the noise signal ($S_{Noise}$) are gathered by the anesthetizing monitoring unit within an adjacent time interval ($T_{Noise}$) not overlapping with the stimuli signal interval ($T_{Stimulus}$) and the duration of the response signal ($T_{Response}$).

12. An anesthetizing monitoring unit with stimulating electrodes, receiving electrodes, a memory, and a display configured to generate an improved evoked electromyography response signal ($\Sigma_{Response}$), the anesthetizing monitoring unit comprising:
an input port,
an output port, and
processing circuitry being configured to:
  generate a single stimuli signal ($S_{Stimuli}$), wherein the single stimuli signal ($S_{Stimuli}$) comprises a single pulse and is configured to stimulate a motor nerve of a patient,
  output the generated single stimuli signal ($S_{Stimuli}$) to the stimulating electrodes on the patient using the output port of the anesthetizing monitoring unit,
  receive a single evoked electromyography, EMG, response signal ($S_{Response}$) from the receiving electrodes on the patient at the input port of the anesthetizing monitoring unit, having a duration ($T_{Response}$), in response to the outputted stimuli signal ($S_{Stimuli}$),
  estimate a periodic noise waveform ($S_{Periodic}$), having the duration ($T_{Response}$), based on a noise signal ($S_{Noise}$) by splitting the noise signal ($S_{Noise}$) into temporal segments, wherein:
    the noise signal ($S_{Noise}$) is caused by an electric power grid having a frequency;
    the temporal segments each have a periodic duration ($T_{Periodic}$) matching the frequency of the electric power grid; and
    the temporal segments of the noise signal ($S_{Noise}$) are detected during a time interval ($T_{Noise}$) not overlapping with a stimuli signal interval ($T_{Stimulus}$) of the single stimuli signal ($S_{Stimuli}$) and not overlapping with the duration of the response signal ($T_{Response}$),
  generate the improved response signal ($\Sigma_{Response}$) by subtracting the noise waveform from the response signal ($S_{Response}$) to reduce noise in the response signal ($S_{Response}$) caused by the electric power grid,
  store the improved response signal ($\Sigma_{Response}$) in the memory in the anesthetizing monitoring unit, and present the improved response signal ($\Sigma_{Response}$) on the display in the anesthetizing monitoring unit.

13. A computer program is provided comprising computer-executable instructions stored on a non-transitory computer medium for causing an anesthetizing monitoring unit with stimulating electrodes, receiving electrodes, a memory, a display, an input port, and an output port, when the computer-executable instructions are executed on a processing unit comprised in the anesthetizing monitoring unit, the anesthetizing monitoring unit performs the steps of:

generating a single stimuli signal ($S_{Stimuli}$), wherein the single stimuli signal ($S_{Stimuli}$) comprises a single pulse and is configured to stimulate a motor nerve of a patient, outputting the generated single stimuli signal ($S_{Stimuli}$) to the stimulating electrodes on the patient using the output port of the anesthetizing monitoring unit, receiving a single evoked electromyography, EMG, response signal ($S_{Response}$) from the receiving electrodes on the patient at the input port of the anesthetizing monitoring unit, having a duration ($T_{Response}$), in response to the outputted stimuli signal ($S_{Stimuli}$), estimating a periodic noise waveform ($S_{Periodic}$), having the duration ($T_{Response}$), based on a noise signal ($S_{Noise}$) by splitting the noise signal ($S_{Noise}$) into temporal segments, wherein:
- the noise signal ($S_{Noise}$) is caused by an electric power grid having a frequency;
- the temporal segments each have a periodic duration ($T_{Periodic}$) matching the frequency of the electric power grid; and
- the temporal segments of the noise signal ($S_{Noise}$) are detected during a time interval ($T_{Noise}$) not overlapping with a stimuli signal interval ($T_{Stimulus}$) of the single stimuli signal ($S_{Stimuli}$) and not overlapping with the duration of the response signal ($T_{Response}$), generating the improved response signal ($\Sigma_{Response}$) by subtracting the noise waveform from the response signal ($S_{Response}$) to reduce noise in the response signal ($S_{Response}$) caused by the electric power grid, storing the improved response signal ($\Sigma_{Response}$) in the memory in the anesthetizing monitoring unit, and presenting the improved response signal ($\Sigma_{Response}$) on the display in the anesthetizing monitoring unit.

* * * * *